United States Patent [19]

Salviatti

[11] Patent Number: Plant 5,364

[45] Date of Patent: Dec. 11, 1984

[54] CARNATION PLANT

[75] Inventor: Forese Salviatti, Pisa, Italy

[73] Assignee: Dianticola Columbiana Ltda., Colombia

[21] Appl. No.: 315,297

[22] Filed: Oct. 23, 1981

[51] Int. Cl.[3] ..... A01H 5/00
[52] U.S. Cl. ..... Plt./71
[58] Field of Search ..... Plt./71

*Primary Examiner*—Robert E. Bagwill
*Attorney, Agent, or Firm*—Irvin A. Lavine

[57] ABSTRACT

A carnation plant known by the cultivar name Eolo and particularly characterized as to uniqueness by the combined characteristics of commercial double flower type; cupola flower form when open; very small flower size; pink-lilac flower color; 4–7 flowers and buds showing color per flowering stem; strong peduncle strength; short peduncle length; constant number (five) sepals; constant number (thirty-two) petals; petals have insignificant serrations; petal has very long nail; two styles; styles have curly peaks; calyx color somewhat darker than peduncle.

1 Drawing Figure

The present invention comprises a new and distinct cultivar of *Dianthus caryophyllus, L.* hereinafter referred to by the name Eolo.

Eolo is the product of a planned breeding program which had the objective of creating new type carnation cultivars in a wide color range with fast flowering response, unrestricted breaking action, vigorous growth, strong, nonbrittle stems, high bud and flower count, and attractive durable flowers for year round commercial production.

Eolo was originated from a cross made in San Remo, Italy, in the year 1974–1975. The male parent was Minuature Rosa 21/74. The female parent was "Chinensis Rifiorente". Both parents are unpatented.

After several trials of multiplication by vegetative cuttings, Eolo has not shown any alteration, and the new variety is contant.

Eolo has not been observed under all possible environmental conditions. The phenotype may vary significantly with variations in environment such as temperature, light intensity and day length. The following observations, measurements, and comparisons describe plants grown in San Remo, Italy, under greenhouse conditions which approximate those generally used in commercial practice.

The following traits have been repeatedly observed and are determined to be basic characteristics of Eolo which in combination distinguish this carnation as a new and distinct cultivar:

1. Commercial double flower type
2. Cupola flower form when open
3. Very small flower size
4. Pink-lilac flower color
5. Fast flowering response
6. 4 To 7 flower buds showing color per flowering stem
7. Strong peduncle
8. Short penduncle length
9. Number of sepals constant; five
10. Number of petals constant; thirty-two
11. Petal edges have insignificant serrations
12. Petals have very long nail
13. Flower has constant number of styles; two
14. Styles have curly peaks;
15. Calyx color somewhat darker than peduncle
16. Pagina of petals not very much developed.

No carnations known to the present inventor is similar to Eolo. A comparable or similar carnation, to the knowledge of the inventor, does not exist.

The accompanying photographic drawing is a color photograph showing typical inflorescence and foliage characteristics of Eolo. Colors are as nearly true as possible with illustrations of this type.

In the following description, color references are taken from A Limit Color Cascade (Munsell).

CLASSIFICATION

Botanical: *Dianthus caryophyllus,* L. Eolo.

Commercial: Spray carnation for cut flower production.

INFLORESCENCE CHARACTERISTICS

Flowering response: Blooms from seed in approximately forty days; pinch to bloom in approximately twenty days.

Inflorescence type: Semi-compound spray, with one bud per lateral.

Number of buds and flowers per stem: 4 To 7.

Peduncle length: 25–35 cms.

Peduncle strength: Strong.

Flower:

*Size.*—Small, 3.8 cms.

*Type.*—Commercial double, petals from 20–39 in number (winter); average approximately 32.

*Form.*—Cylindrical as a bud; opens to cupola.

Corolla color:

*General tonality from a distance of* 3 *meters.*—Pink-lilac, near 44-4, paling to 44-3 towards center. The bud, prior to complete opening, has a color near 44-6, 44-7. Reverse, between 44-2 and 44-3.

Keeping quality: Excellent. As a cut flower, keeps up to ten days under room temperature.

Fragrance: Typical carnation fragrance, reminiscent of vanilla.

PLANT CHARACTERISTICS

Growth and duration: Vigorous, high number of stems.

Branching pattern: Numerous and unrestricted at base of plant.

Height: Miniature.

Stem: Strong, having a total of 7 internodes under calyx and of short length, with dark green color; when cut transversely in the middle of longest internode, stem is round. Stems are erect and rigid.

Foliage:

*Occurence.*—Abundant; typical carnation; leaves have short length, and medium width.

*Color.*—Green, normal for carnations.

I claim:

1. A new and distinct cultivar of *Dianthus caryophyllus, L.* known by the cultivar name Eolo, as described and illustrated, and particularly characterized as to uniqueness by the combined characteristics of commercial double flower type; cupola flower form when open; very small flower size; pink-lilac flower color; 4 to 7 flowers and buds showing color per flowering stem; strong peduncle and short peduncle length; five sepals; thirty-two petals; petals having insignificant serrations and long nail.

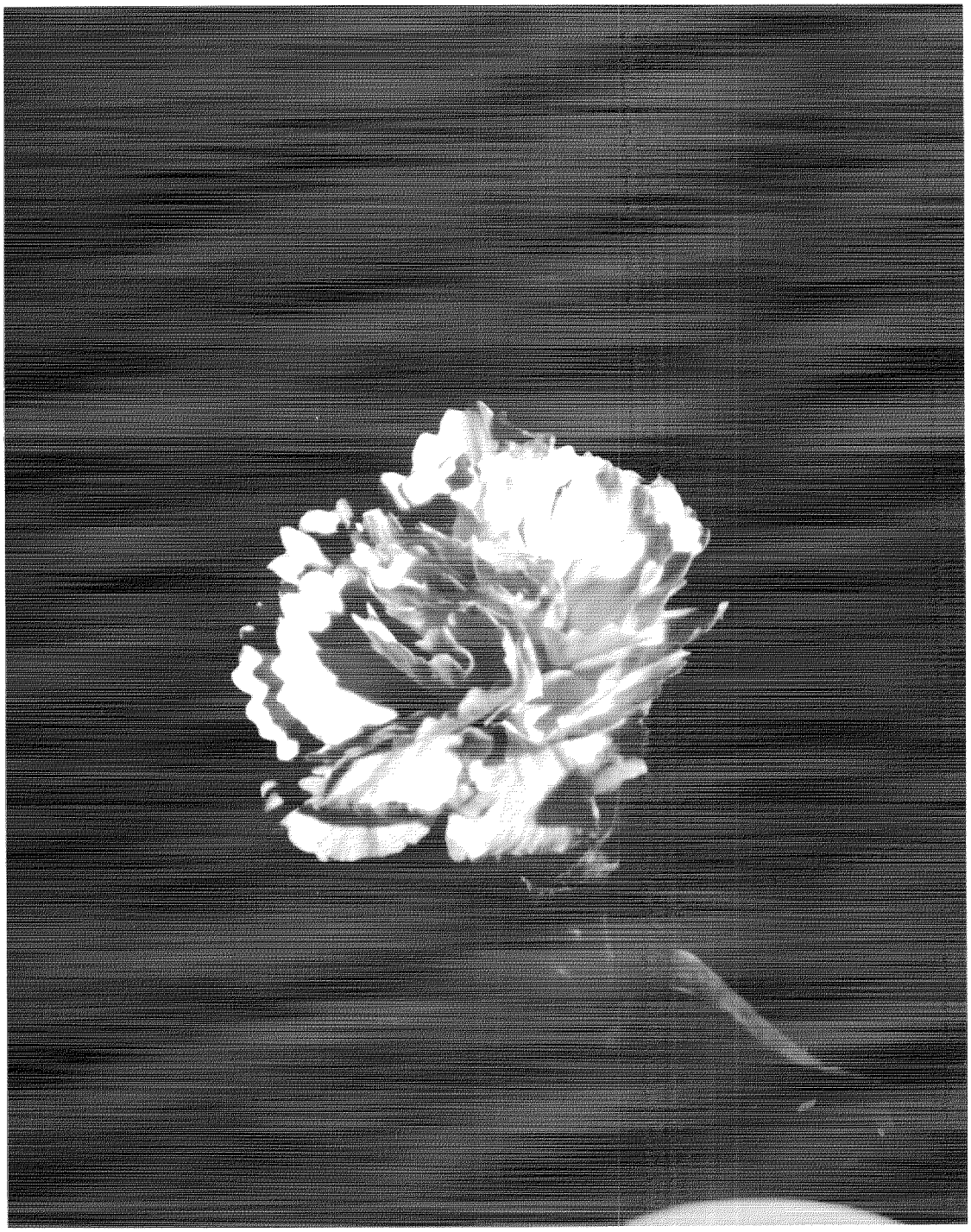

* * * * *